Figure 1:
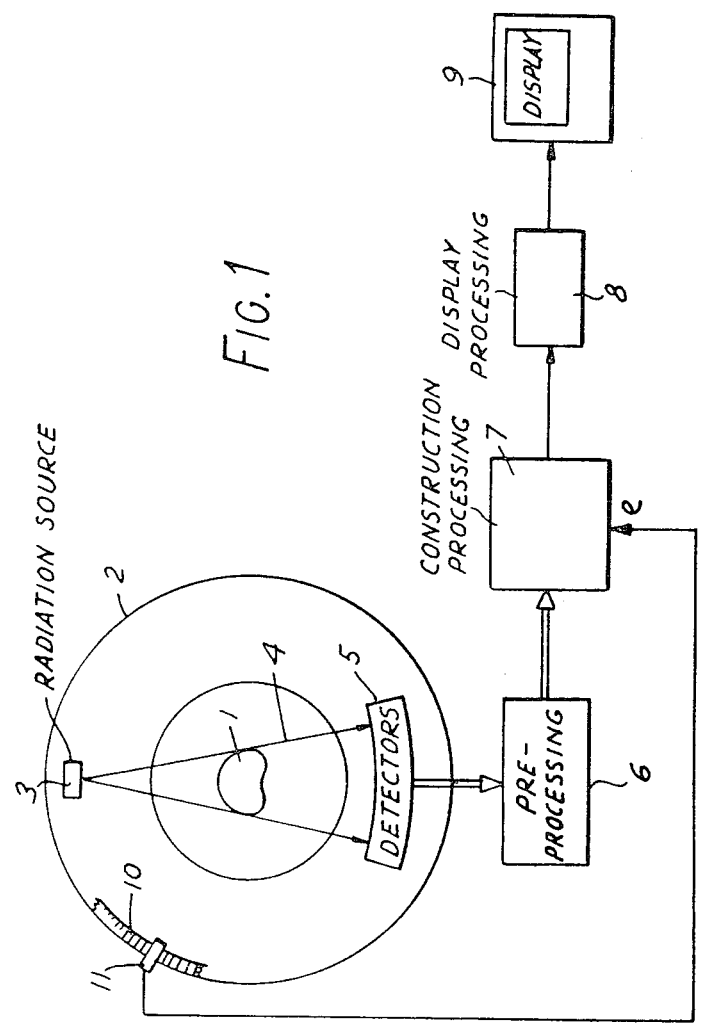

United States Patent [19]

Watson

[11] 4,274,140
[45] Jun. 16, 1981

[54] ARRANGEMENTS FOR CONSTRUCTING REPRESENTATIONS OF PARTS OF BODIES

[76] Inventor: David M. Watson, 17, Latchmoor Way, Gerrards Cross, Buckinghamshire, England

[21] Appl. No.: 37,530

[22] Filed: May 9, 1979

[30] Foreign Application Priority Data

May 12, 1978 [GB] United Kingdom .............. 19149/78

[51] Int. Cl.$^3$ ............................................ G06F 15/42
[52] U.S. Cl. ............................... 364/414; 250/445 T; 364/515
[58] Field of Search ............................. 364/414, 515; 250/445 T, 363 S; 358/111

[56] References Cited

U.S. PATENT DOCUMENTS

| | | | |
|---|---|---|---|
| 3,778,614 | 12/1973 | Hounsfield | 250/362 |
| 3,924,129 | 12/1975 | LeMay | 250/336 |
| 4,002,910 | 1/1977 | LeMay | 250/445 T |
| 4,010,371 | 3/1977 | LeMay | 250/445 T |
| 4,035,647 | 7/1977 | Hounsfield | 250/445 T |
| 4,044,240 | 8/1977 | Cox, Jr. et al. | 250/445 T |
| 4,075,483 | 2/1978 | Trancrell et al. | 250/363 S |
| 4,138,611 | 2/1979 | Hounsfield | 250/445 T |
| 4,144,570 | 3/1979 | Wagner | 364/414 |
| 4,149,250 | 4/1979 | Jass | 250/445 T |
| 4,168,435 | 9/1979 | Duinker | 250/445 T |

FOREIGN PATENT DOCUMENTS 2521796 11/1976 Fed. Rep. of Germany ........... 364/414

OTHER PUBLICATIONS

Herman et al.; "Reconstruction Using Divergent-Ray Shadowgraphs"; *Reconstruction Tomography in Diagnostic Radiology and Nuclear Medicine;* Ed. Ter-Pogossian et al., pp. 105–117.

*Primary Examiner*—Errol A. Krass
*Attorney, Agent, or Firm*—Cooper, Dunham, Clark, Griffin & Moran

[57] ABSTRACT

In a CT scanner system electrical signals are provided for radiation paths in a fan-shaped distribution through a region of interest of the patient. The signals are processed and further signals derived therefrom are mapped onto elements of a matrix defined in the region by being summed in storage locations corresponding to the elements. The mapping includes weighting by a factor related to the angle of the respective beam in the fan, the factor being different for each matrix element. To achieve more efficient use of the circuits handling the signals it is proposed to stretch the signals onto a line parallel to lines of matrix elements applying an angular part of the weighting common to all of the rows and leaving a straightforward stepping through the signals to be followed as they are allocated to the storage locations.

9 Claims, 7 Drawing Figures

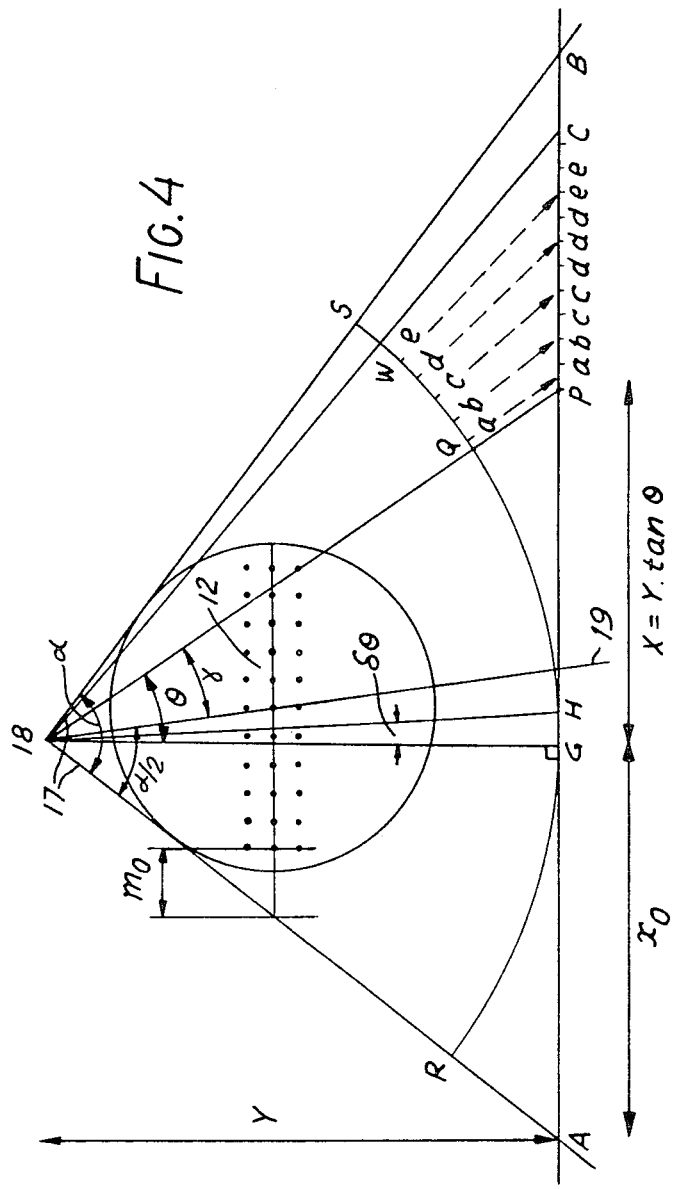

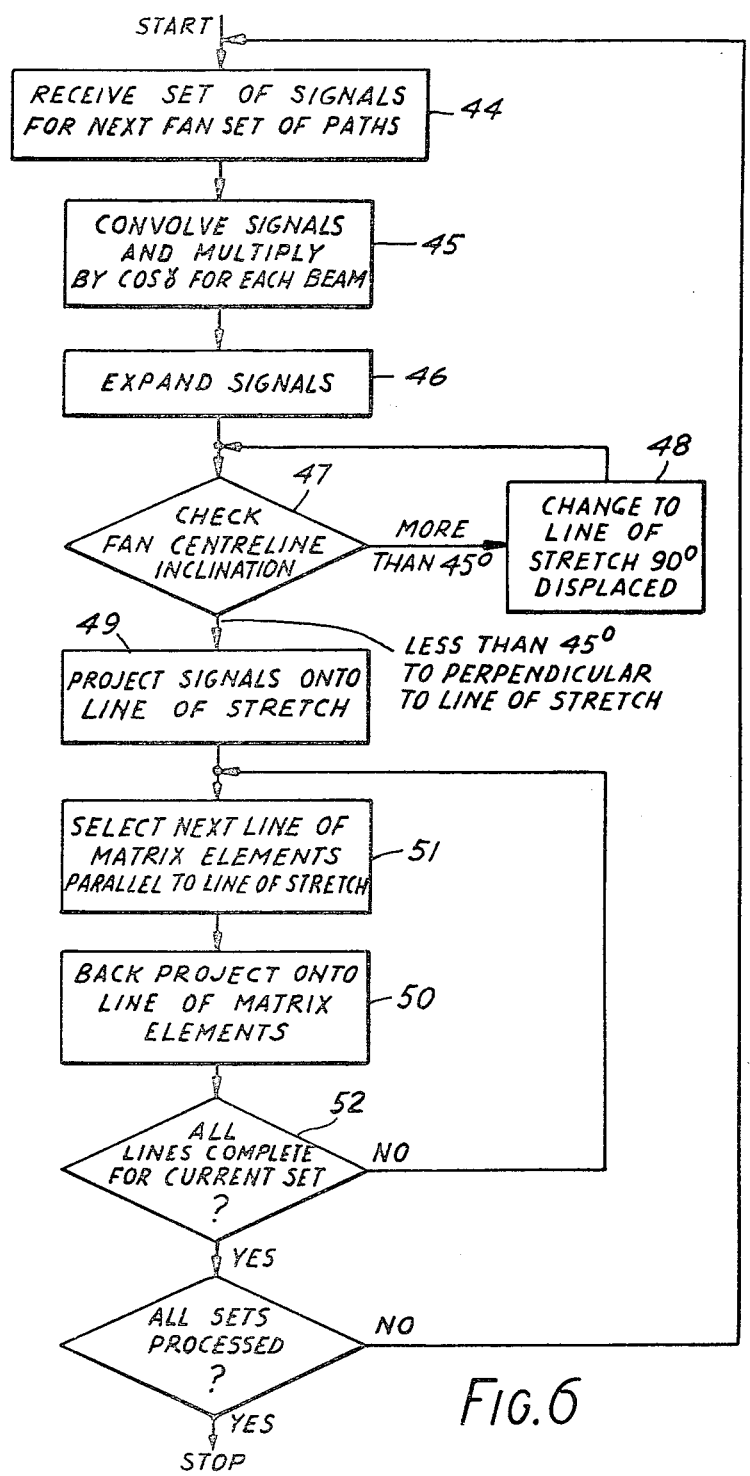

ARRANGEMENTS FOR CONSTRUCTING REPRESENTATIONS OF PARTS OF BODIES

The present invention relates to the processing of signals representing measurements of a quantity in a region of interest, to construct a representation of the distribution of the quantity in the region. It is particularly related to the processing of measurements of attenuation of penetrating radiation, in a slice of a patient, to derive a representation of the distribution of attenuation of the radiation with position in the slice.

In U.S. Pat. No. 3,778,614 there is described apparatus known as computerized tomographic (CT) apparatus, for obtaining and processing such measurements of attenuation. The apparatus includes a source of penetrating radiation and detector means responsive to the radiation. The source and detector means are scanned, in the slice and relative to the body, so that the detector means provides output signals which, after pre-processing steps, can be processed to give the desired representation. The said United States patent describes a suitable method for processing the signals. An improved form of the processing is described in U.S. Pat. No. 3,924,129. As described in both Patents the detector output signals are organised into sets, each of which can conveniently comprise attenuation values, relating to corresponding paths of a set of paths of the radiation through the slice being examined. Each set is then operated upon so that each signal is modified by combination with contributions from other signals. The modified signals are "mapped" into storage locations corresponding to elements of a matrix of elements notionally defined in the slice. The distribution is such that each location holds the sum of all modified signals for radiation paths the centre lines of which pass through the corresponding element in the slice. To ensure that the distribution to each storage location is related to the extent of interception of the element in the region of interest by the beam paths, the modified signals are interpolated to provide a larger number of signals corresponding to attenuation of radiation in respective ones of an increased number of radiation paths.

Although the sets of detector output signals can conveniently correspond to sets of parallel paths, this is not necessary. In some forms of CT apparatus, described for example in U.S. Pat. No. 4,035,647, examination is by sets of radiation beams distributed in a fan originating at the radiation source. It is then convenient to process the signals for fan distribution of paths corresponding to different positions of that fan of beams. This can be achieved using the said processing but, if the embodiment of the processing based on said U.S. Pat. No. 3,924,129 is employed, consequential additional modifications are required as the modified signals are distributed to the corresponding storage locations. Suitable modifications for such processing have been described in U.S. Pat. No. 4,010,371 and a theory of such modifications has been described by Herman, Lakshminarayanan and Naparstek "Reconstruction using Divergent-Ray shadowgraphs" from "Reconstruction Tomography in Diagnostic Radiology and Nuclear Medicine" ed. Ter. Pogossian et. al PP 105-117, 1977, University Park Press Baltimore, Md. U.S.A. and others. The distribution of the additionally modified signals to the required storage locations can be achieved without undue difficulty but the stages to be followed are relatively inefficient in organisation of the paths which the signals follow through the processing and can result in long processing times. It is an object of this invention to provide a method of achieving the distribution which is more efficient.

It is another object of the invention to provide an apparatus for processing electrical signals derived from a computerized tomographic scanner and relating to attenuation suffered by x-radiation on traversing each of many substantially linear paths across a cross-sectional slice of a body under examination, said scanner supplying the signals in groups relating to sets of paths, the paths of each set diverging from a focus and the focus for each set being disposed at a different angular location relative to the cross-sectional slice and the signals in each group being supplemented as required by signals, formed by interpolation between the first mentioned signals, to represent attenuation for divergent paths not actually irradiated, the processing apparatus including a matrix store having a plurality of locations each of which is allocated to one of a plurality of elemental regions of the body, said elemental regions being disposed in a rectangular array in said slice; means for selecting and distributing to the locations of the matrix store contributions from the signals, both measured and interpolated, relating to paths traversing the corresponding elemental regions of the body; the means for selecting and distributing including;

(a) a further store having a plurality of locations, representing a plurality of equally spaced positions on a line defined as being parallel to a plurality of parallel lines of the elemental regions, (b) means for distributing the constributions from the signals of a group to the locations of said further store, each location receiving that contribution relating to the path passing closest to the corresponding one of said spaced positions, and, (c) means for distributing at least a part of the contribution in said location, of the further store, to locations of the matrix store, corresponding to elemental regions of the body intersecting a line joining the corresponding one of said spaced positions to the said focus.

Figure 2:
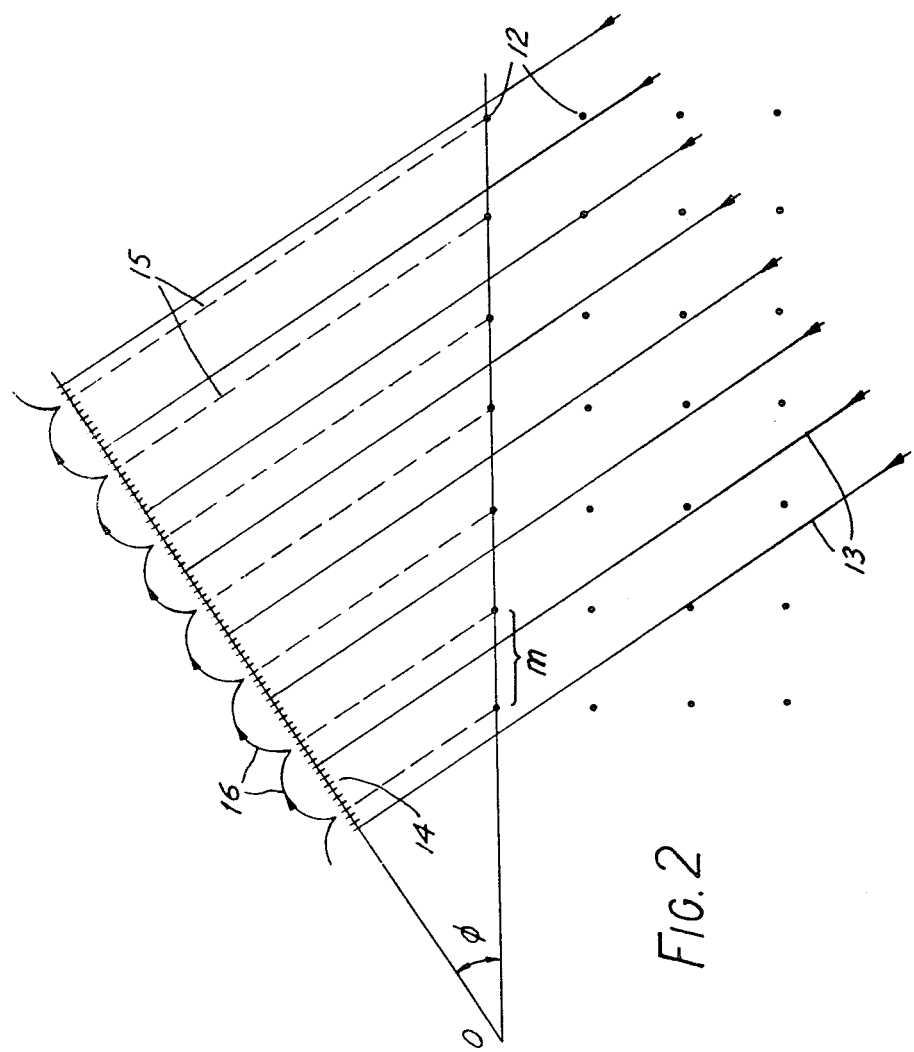
Figure 3:
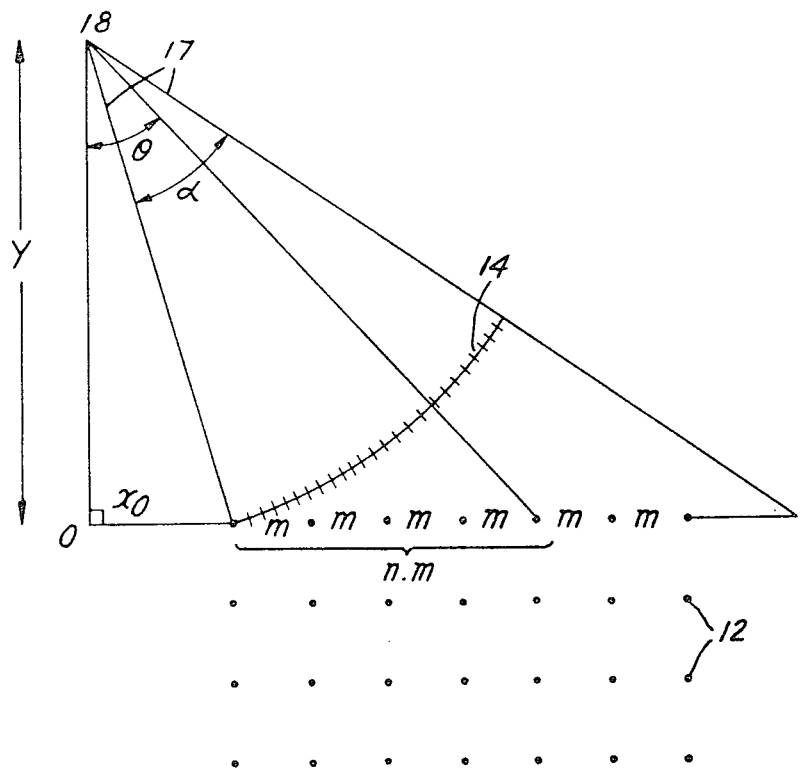
Figure 5A:
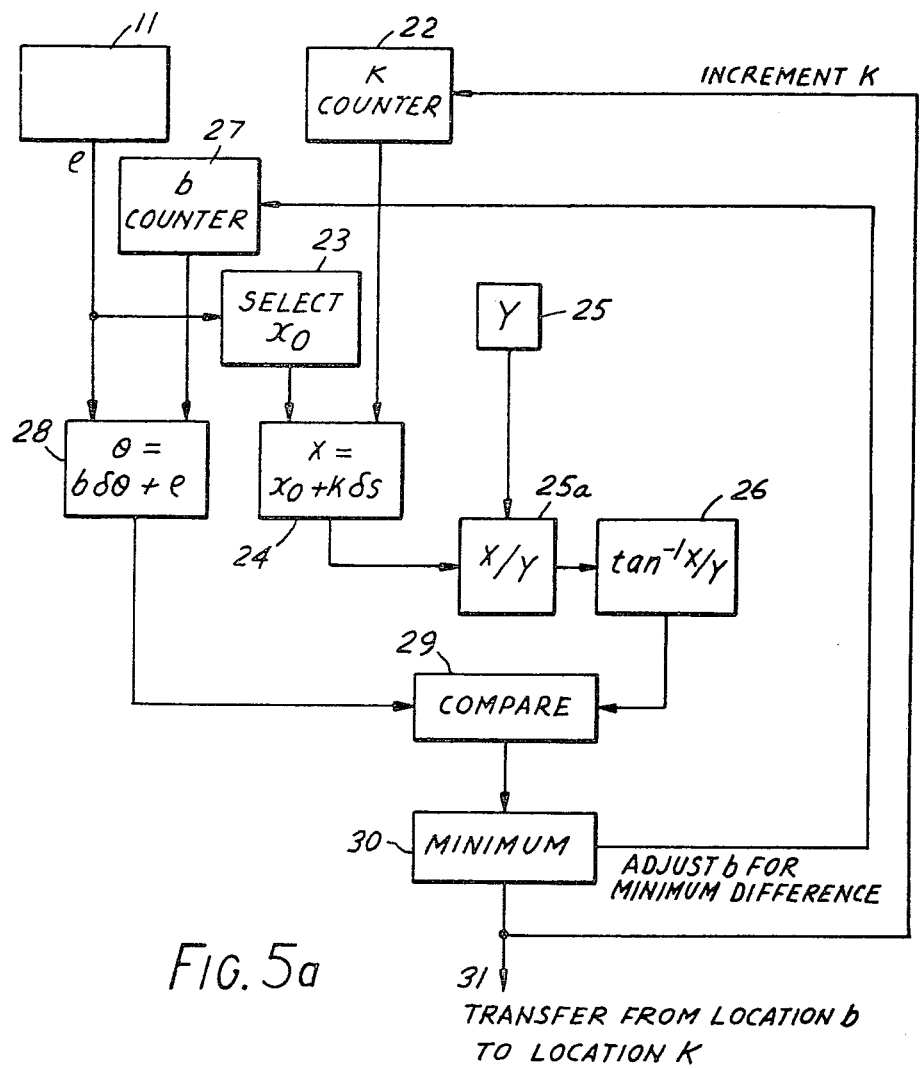
Figure 5B:
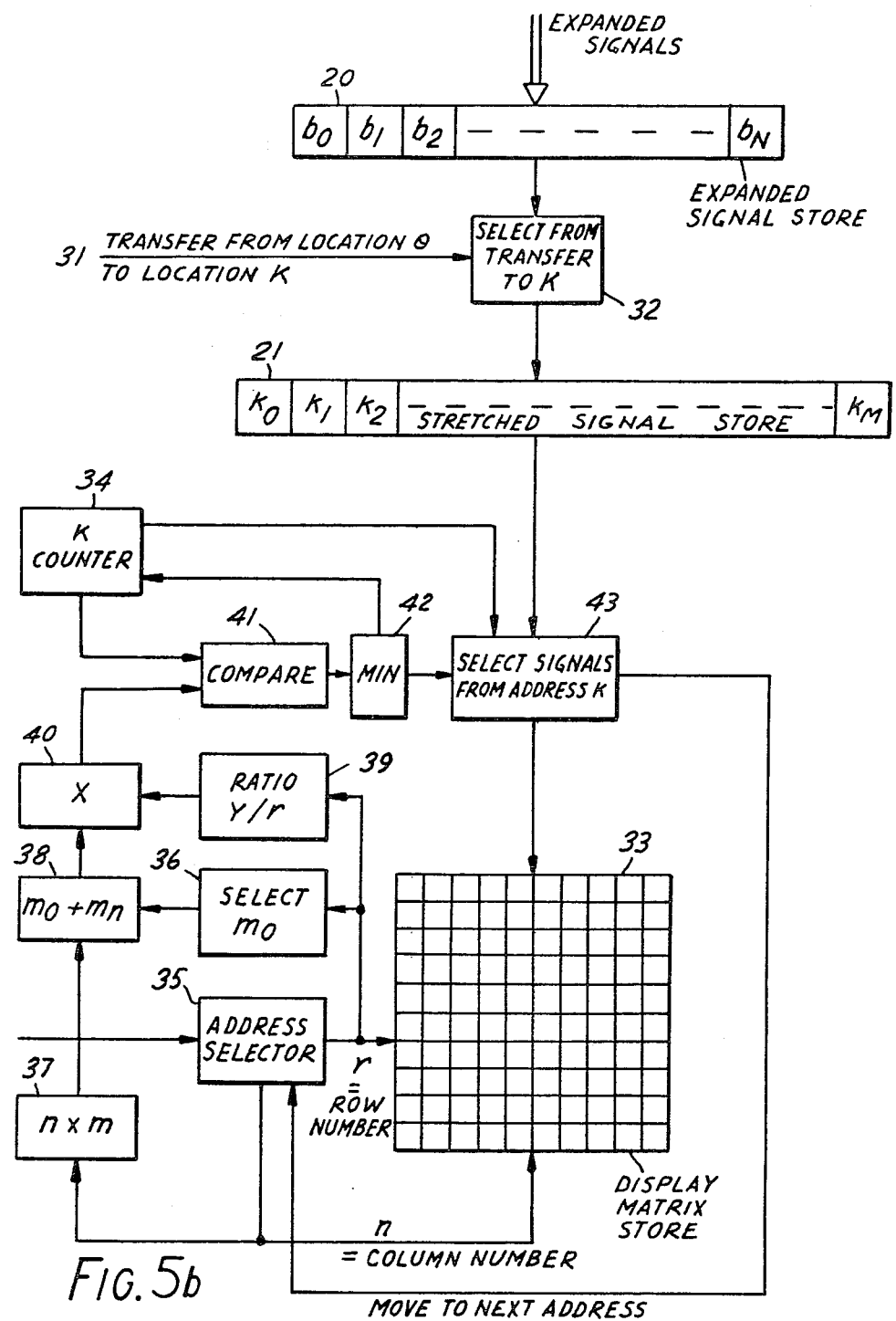

In order that the invention may be clearly understood and readily carried into effect, it will now be described by way of example, with reference to the accompanying drawings, of which:

FIG. 1 illustrates in simplified form a CT apparatus embodying the invention,

FIG. 2 shows a known method of back-projection of signals relating to parallel beam paths, FIG. 3 is used to explain the problems resulting from back projecting signals representing fan distributions of beam paths, FIG. 4 is used to explain the present method of back-projecting signals representing fan distributions of beam paths, FIG. 5a and 5b are block diagrammatic circuits of one embodiment of part of the FIG. 1 apparatus, and FIG. 6 is a flow diagram showing the sequence of back-projection used in this invention.

FIG. 1 shows in diagrammatic form a CT apparatus embodying this invention. Output signals, relating to the attenuation of radiation in a body 1, are obtained in a scanning apparatus indicated generally at 2. This scanning part, which includes source 3, directing a fan distribution of radiation 4 through body 1, and detectors 5, receiving the radiation, is illustrated as the type described in U.S. Pat. No. 4,035,647 which is hereby incorporated by reference in this application. It can, however take other suitable forms known for CT apparatus, for example that described in United States Patent Application Ser. No. 772,689 filed in Feb. 28, 1977, in the name of Colin C. Oliver and assigned to EMI Limited. The output signals are preprocessed by circuits 6, in which they are, for example, converted to logarithmic and digital form, to take the form of measurements of attenuation of the radiation for the paths along which it has passed through the body. The signals representing these measurements are then processed in circuits 7 to provide the desired reconstruction of the distribution of attenuation in the examined slice. The processed signals, which now represent attenuation values for elements of the said matrix, are further subjected to display processing in circuits 8 to be provided in a form compatible with a chosen display unit 9. This invention is, however, concerned primarily with the construction of processing circuits 7 and the subsequent display processing will not be further described.

Circuits 9 require information indicative of the progress of the rotational scan. For this reason the apparatus includes a graticule (shown in part at 10) which co-operates with a photocell unit 11 to provide processing circuits 7 with signals which represent orbital step $p$.

It has been mentioned that the processing can be based on a technique described in U.S. Pat. No. 3,924,129 and the disclosure therein is hereby incorporated by reference. In the following description it will be assumed that the signals are arranged in sets and the signals of each set have been modified by subtraction of contributions from other signals of the same set and have been interpolated, or "expanded" to produce a larger number of intermediate signals interposed between successive pairs of the original signals. There are, therefore, in each set a plurality of signals relating to a sufficiently large number of paths distributed in a fan, originating at a focus which may be one position of the radiation source or may be a notional focus defined by the scanning used, as defined in United States Application Ser. No. 934,311 filed Aug. 17, 1978, now U.S. Pat. No. 4,078,511 in the names of Godfrey N. Hounsfield and Richard M. Waltham, and assigned to EMI Limited. The focus may also be at a signal detector looking at a number of source positions as is possible with the apparatus described in the above-referenced United States Application Ser. No. 772,689. The invention is then concerned with the distribution of the signals to storage locations corresponding to matrix elements, a procedure known as "back-projection". It should be mentioned that, if the modification of the signals is carried out in accordance with a so-called convolution function appropriate for parallel beam paths, use with signals for a fan distributed set of beam paths requires additional modification of each signal as it is back projected, in accordance with a function of D, the distance of the respective element from the fan focus. In a preferred procedure the function is proportional to $1/D^2$ and a further modification is required dependent on the cosine of the angle of this beam in the fan from the bisector of the fan. A theory of the modification for fan distributions of the beam paths may be found, inter alia, in said reference "Reconstruction Using Divergent-Ray Shadowgraphs".

One aspect of the processing required for back projection may be more clearly seen from consideration of the simpler case of back projection of signals for parallel beam paths. For the purposes of explanation of this there is shown in FIG. 2 a simplified view of the geometry of that case. In that Figure there can be seen part of the cartesian matrix of elemental areas, in the region of the body 1 being examined; each elemental area is considered to be a solid element with rectangular sides and is denoted by its centre point 12. Each point 12 has a corresponding storage location in a so-called matrix store in which the representation is to be assembled and the signals are to be organised in the store in a manner simulating the procedures to be described.

The matrix elements are spaced at separation m and are intersected by beams of radiation which are indicated at 13 by their centrelines. The beams may be of beam width equal to the distance between their centrelines or may in fact overlap. Sets of beams such as that shown intercept the body at many different orientations for a single examination. The normal to the set shown is inclined at an angle $\phi$ to the matrix rows. The back projection procedure requires that for each storage location there is summed the modified absorption data for all beams, one for each such set, the centre lines of which passes through the corresponding matrix element. If the centre of an element is actually intersected by a beam (as identified by its centreline) for the set shown the modified attenuation signal is applied with full weight. If however, the centre line does not pass through the centre of an element, the modified attenuation signal is applied with a weight (less than unity) dependent on the distance of the centre line of the beam from the centre of the element. To achieve the desired weighted values, the signals are interpolated to provide intermediate values appropriate to notional interpolated beams having centre lines lying between those of the real ones. A sufficient number of interpolated values are provided to ensure that one notional or real beam passes at least close to the centre of each matrix element. The positions of the centre lines of interpolated beams are shown in FIG. 2 at 14. The interpolation may be effected in conformity with a suitable interpolating function.

The signals could be allocated to the storage locations in any desired order. However it is desirable to adopt a sequence which is efficient in use of signal paths in the electronic circuits used. It is therefore desirable to back-project at one time into a well defined group of storage locations, which may typically represent a row, column or even a diagonal of the matrix elements. For example each storage location corresponding to the upper row of centre points in FIG. 2 receives, from the set of beams shown, a value for the respective notional beam shown by a broken line 15, which is extrapolated from one of the positions 14.

The set of interpolated (expanded) signals is held temporarily in respective storage locations in a store for the interpolated signals storage in the processing unit 7 (after modification and interpolation) and the back-projection involves stepping through the stored values for a set from an arbitrary point and transferring the signals from the store for the interpolated signals to the matrix store. If the stepping is set to start from an arbitrary origin 0, conveniently the centre of rotation of the scanning means 2 then, after an initial adjustment, the addresses of the matrix store and stepped through by the circuit in equal increments or steps of m units and this will be the same for each matrix row or column. To keep step the interpolated-signal store addresses must step through equal increments 16 of m cos $\phi$. The magnitude cos $\phi$ is the ratio of the distance between the centres of adjacent matrix elements to the distances between the centre lines of the beams represented by the expanded signals. This will change for a different beam path set at a different angle φ but it is at least constant for one set and need only be recalculated for a change of set. In practice a value of Cos φ will be provided from a memory in the circuit 7 organized to operate as a look-up table for a value of φ provided by sensors on the CT equipment. At each step the corresponding signal is transferred from the current address in one store to the current address in the other.

The procedure so far described for parallel sets of beam paths has been used in practice in the CT scanners manufactured and sold by EMI Medical Ltd and EMI Medical Inc. and is well understood. It is, therefore, preferable to use a similar procedure for fan distributed sets of beam paths.

FIG. 3 shows the simplified geometry of the fan arrangement, having the same matrix of elements represented by the centre points 12 intercepted by a fan distribution of beams (not shown individually) extending between limits 17, over an angle α from a focus 18. The expansion process is the same as for parallel sets but now produces a group of modified and interpolated absorption signals equiangularly disposed on an arc about 18 (as represented by 14) to relate to their respective real or notional beams, it being understood that as for the other figures the numbers of absorption measurements and matrix elements are much reduced from typical values, for the sake of clarity.

The procedure for back projecting the signals to the matrix store may be essentially the same as in the parallel set case but, for equal steps of address along the matrix row, the interpolated signal store address is stepped by different increments related to angle θ, which is the angle of an individual fan beam, notional or real, to the matrix columns. It will be seen that on proceeding away from the origin 0 each successive step in numbers of signal values 14 will be smaller. If the addresses in the store for interpolated or expanded signals are identified by values of θ, which is convenient, then for a matrix element $x_o+nm$ from 0 the correct interpolated value to be selected and applied to the respective storage location in the matrix store can be determined by the equation $\theta = \tan^{-1}[(x_o+nm)/y]$ from 0. This can be determined as before with the aid of a memory organised to operate as a look up table but the arctangent memory must be accessed for each step (since the equation is dependent on n, the number of steps) and this is a time consuming procedure.

In practice the back-projection for a row of matrix elements is accomplished under control of a circuit which is repeatedly operated to route the signals appropriately for each different row and each different set of beam paths. This invention reorganises the interconnections of the processing circuits so that the look-up tables for arc tangent need only be accessed once for the back projection of a set to all the storage locations of the matrix store and not for each storage location.

FIG. 4 used to explain the geometrical considerations underlying this invention shows a fan of angle α disposed about a centre line 19. As in FIG. 3 the modified and interpolated signals can be considered to be for beam paths disposed at equal spacing along arcs RGQWS. As mentioned before, in one arrangement this arc can represent a line of detectors on an arc centred on an x-ray source at 16. It is desired to back project the interpolated signals into storage locations corresponding to matrix elements 12, of which three rows are shown. It is proposed to first project the signals onto a line AGHPB, parallel to the matrix row, and tangential to RGQWS, bearing in mind that the actual procedure involves operating on electrical signals in simulation of the geometrical procedures described. The line AGHPB is at a distance Y from the fan focus or virtual focus 18 and the angle θ of a beam is defined from the line from focus 18 to point G. Also defined is the angle α which is the angle between the centreline of a beam and the centreline (bisector) 19 of the fan angle 8. With these definitions, back projection is exactly as explained in relation to FIG. 3, with each successive step along the interpolated value locations on RGHQS requiring access to arctan lookup tables, as GQ=arctan (X/Y). Two further conditions are imposed, however. The first is that all of the interpolated signals for beam paths on RGHQS are projected on to AGHPB along corresponding radii originating at 18, not merely those passing through one row of matrix elements. The second condition is that the locations to which they are projected are equally spaced along AGHPB although the equiangular lines of projection are not so equally spaced.

The definition used is that for section GH, where the small arc on δθ is close to a straight line, the locations on the line correspond with sufficient accuracy to the equally spaced locations on the arc. They are then extended to A and B at the same spacing. The projection is carried out so that for each location on AGHPB there is selected the interpolated signal corresponding to the beam projected along the nearest equiangular radius. This procedure, shown for a limited number of interpolated values (labelled a to e) between Q and W means that at the extremes of AGHPB several locations receive the same value. For this reason the procedure is called "stretching".

Having projected the interpolated signals onto AGHPB, they are then back-projected into the storage locations of the matrix store corresponding to the elements of the parallel matrix rows. In this back projection, in conventional manner, only the stretched values for the notional fan beam closest to each matrix element is back-projected in each case.

The back-projection as before includes stepping the addresses in the matrix store in equal increments along the matrix elements and similarly stepping the corresponding addresses in the store for the "stretched" signals in increments along A to B, transferring the appropriate values. In this case, however, the spacing of matrix elements in any one line corresponds to equal numbers of steps along AGHPB. Although there are different numbers of steps for different matrix rows, the change required is simply in the ratio of the distance of the row along the line from the fan focus 18 to point G.

It will be apparent that the effects of stretching the detector output signals onto AGHPB and then back projecting along matrix rows are that: the arctan lookup tables are accessed only once for each interpolated signal, the steps for each matrix row are of equal value and the steps from one matrix row to the next, for one fan set of beams, are in a simple ratio.

Although FIG. 4 shows only one fan set of beams it should be understood that signals for many such sets of beams are stretched onto the same line AGHPB, which can be called the line of stretch. When the fan centre line exceeds 45° from the perpendicular to the line of stretch, a new line of stretch, 90° displaced, is used and back-projection is onto the matrix columns. If desired an intermediate line of stretch may be used to back-project into storage locations corresponding to matrix diagonals. The relevant consideration is that, for any sequence of storage locations into which the signals are to be back-projected, the line of stretch is parallel to that sequence. Although in FIG. 4 it is shown external to the matrix of elements 12, in a preferred embodiment the line of stretch is one such row, column or diagonal, preferably central to the matrix. It should also be mentioned that it is important that the modified values are interpolated or expanded onto arcs such as RGHQS prior to stretching and not expanded onto the line of stretch.

Whereas FIGS. 2 to 4 were simply explanatory of the geometry of the arrangement, FIGS. 5a and 5b, which will be explained with reference to FIG. 4, show an actual circuit for implementing the organisation of signal paths according to the invention for signals for a sequence of fan sets of beam paths within the required angle of one line of stretch. It will be understood that the sequence is restarted with a new line of stretch when $\theta$ exceeds a suitable value. Successive sets of signals correspond to adjacent fan sets of beam paths whose median lines 19 are spaced at angular increments $\rho$. A value of $\rho$ for each set is provided by the photocell unit which indicates the current scan position.

The expanded values are considered to be for beam paths, along lines RGHQS starting at R and are in fact held in a store 20. Each value corresponds to a value of $\theta$, which is the inclination of the respective beam to the perpendicular to the line of stretch. Thus the FIG. 4 arrangement values of $\theta$ between R and G will be negative. However $\theta$ is defined in the circuit as $b\, \delta\theta + \rho$ where $\delta\theta$ is the step between adjacent beam paths and b has the value 0 at R and N at S. Each signal in store 20 can thus be labelled with its b value as $b_0, b_1 \ldots b_N$.

The signals are to be stretched onto line of stretch AGHPB by being entered into store 21 at locations corresponding to positions, on the line of stretch, spaced at $\delta s$. Each position is at a distance X from point G where $X = x_0 + k\, s$ so that X is stepped in response to the stepping of integer k from 0 to M. Similarly the signals are in locations labelled $k_0$ to $k_M$.

The arrangement is such that k is stepped regularly from A to B and b is stepped from 0 to N in response to the changes in k. The signal in the location of the current b value in 20 is transferred to the location in 21 having the current k value.

As explained before some expanded signals are used more than once as stretched signals and therefore b is not stepped each time k is stepped.

FIG. 5a shows a circuit for deriving control signals which control the transfer of detector output signals after interpolation or "expansion". Counter 22 holds the current value of k. For each set of signals there is a predetermined $x_0$ which is supplied by a store 23 in response to the $\rho$ input from 11, identifying the set. Combining inputs from 22 and 23, unit 24 determines the current value of $X = x_0 + k\, \delta s$. This is supplied together with the value of Y, which preset for the equipment is held in read only memory 25, to divider 25a which provides X/Y. Unit 26, organised as a look-up table provides $\tan^{-1} X/Y$ from the X/Y input. This gives in effect the angle of the notional beam path going through the current stretched point. The current b value is held in a counter 27 and a unit 28 takes the values of b and $\rho$ and provides the corresponding $\theta$ from $\theta = b\delta\theta + \rho$. Unit 29 compares this with $\tan^{-1} X/Y$ and gives the result to unit 30. Unit 30 detects a minimum on the output 29 and instructs counter 27 to change the value of b until it is achieved. Such arrangements are well known. When the minimum is achieved the corresponding values of b and k are provided at 31.

Turning now to FIG. 5b which shows the circuits which actually handle the detector output signals, the b and k values are provided to address selector 32 which effects the transfer from corresponding locations in store 20 to store 21.

The next stage is to project the signals onto locations, in a matrix store 33, which correspond to matrix elements. There are, of course, many more locations than indicated in FIG. 5b. The transfer is essentially the same as that just described for stores 20 and 21 except that store 33 is two-dimensional, that is to say it includes storage locations corresponding to each element of the Cartesian matrix notionally delineated in the region of interest. A further counter 34 steps through k as before (but independently of and subsequent to 22). The problem is then to achieve a value of k for each matrix element location corresponding to a stretched signal for a beam path therethrough. An address selector 35 selects a matrix location in store 33 identified by a row number r and a column number n; the selector 35 is preset to increment along a row and then to return to the start of the next row. From FIG. 4 it will be seen that each row has a different value of $m_o$ (the distance of the first location to the beam from 18 through R and A). A store 36 provides the value of $m_o$ from each r. As described hereinbefore the matrix elements are spaced by distance m so that each element is identified by $m_o + mn$. A multiplier 37 provides $n \times m$ from the n input and adder 38 provides $m_o + mn$. In fact the matrix elements are at constant spacing but the beam paths are divergent. Thus to relate to the stretch points k an expansion factor, the ratio of distance Y to row number r (which is effectively the mean radius from 18), is required. This is provided by divider 39 and multiplier 40 multiplies the output of 38 by this factor.

The output of 40 is the quantity indicative of the real or notional beam through the matrix element which can be compared with k to identify the correct location in store 21. As before they are compared, in a comparator 41, and a minimum detector 42 increments k to the required value. When the correct k value has been found address selector 43 locates the corresponding data value in store 43 and applies it to 33. Selector 43 also instructs address selector 35 to change to a new matrix location.

In the present example the line of stretch is assumed to be rotated through 90° when the centreline of the fan assumes angles of value 45°, 135°, 255° and 315° to the perpendicular to the line of stretch in current use. The circuit 7 includes means for switching the row and column control address circuits for each change of angle of the stretch line. The switching means have not been illustrated.

As mentioned hereinbefore, the back-projection described is one stage of the processing represented by block 7 in FIG. 1. The exact nature of the circuits to achieve the procedure required is not limited to one particular form but can be varied to suit the circuits or other processing facilities available. The important consideration is that the back-projection should be performed in the sequence described. To further aid in understanding the operation of the construction processing FIG. 6 is a flow diagram illustrating the operation performed by the block 7.

The processing shown in FIG. 6 is performed on each set of signals in turn, recycling until all the sets are processed. As the set of signals is received (44) it is processed with the convolution series in the manner described in U.S. Pat. No. 3,924,129, making due allowance for the fan distribution of the beam paths, to provide modified signals (45). During this procedure each value is weighted by Cos $\gamma$, where $\gamma$ is the angle between the respective beam path and the bisector of the fan. This is in accordance with a preferred convolution method for fan sets but may be dispensed with in some cases.

The data are then expanded (46) to provide sufficient values along the arc (such as RGHQS). This is by interpolation, conveniently the third difference form described in U.S. Pat. No. 4,002,910. If the mean angle of the fan set does not deviate too much from the direction of the chosen line of stretch (47) then the next stage is followed. If it is excessive then the line of stretch is rotated by 90° to be more suitable for the fan for which signals are being processed (48). Having provided a suitable line of stretch, the modified and expanded signals are projected onto that line using the arctangent relation explained hereinbefore and arctangent look-up tables (49). The stretching is performed such that modified and expanded signals are derived corresponding to beam paths distributed at equal spacing along the line of stretch.

Having stretched the signals it is necessary to back project them on to all lines of storage elements in the matrix store parallel to the line of stretch (50) Such lines may be constituted by rows or columns of the storage elements in the matrix store, and also by diagonal lines of the storage elements. Each storage element receives the modified and expanded signal for the position on the line of stretch intercepted by a straight line through the element from the fan focus. The back projection is performed for adjacent lines of elements in sequence (51) until all lines have been dealt with (52). In this example the lines of matrix elements are rows or columns since the line of stretch rotates through 90°. However it can be rotated through 45°, say, every second rotation causing back projection onto diagonal lines of elements. The preferred processing weights each value applied to an element by $1/D^2$, where D is the distance of the element from the respective fan focus. In this example this scaling by $D^2$ is performed as the value is applied to the respective storage location.

When all of the fan sets of attenuation signals have been processed in this way, the procedure is terminated and the representation which has been assembled is available for further processing and display.

What I claim is:

1. An apparatus for processing electrical signals derived from a computerized tomographic scanner and relating to attenuation suffered by X-radiation on traversing each of many substantially linear paths across a cross-sectional slice of a body under examination, said scanner supplying the signals in groups relating to sets of paths, the paths of each set diverging from a focus and the focus for each set being disposed at a different angular location relative to the cross-sectional slice and the signals in each group being supplemented as required by signals which are formed by interpolation between the first mentioned signals to represent attenuation for divergent paths not actually irradiated, the processing apparatus including a matrix store having a plurality of locations each of which is allocated to one of a plurality of elemental regions of the body, said elemental regions being disposed in a rectangular array in said slice; means for selecting and distributing to the locations of the matrix store contributions from the signals, both measured and interpolated, relating to path traversing the corresponding elemental regions of the body; the means for selecting and distributing including;
   (a) a further store having a plurality of locations, representing a plurality of equally spaced positions on a line defined as being parallel to a plurality of parallel lines of the elemental regions,
   (b) means for distributing the contributions from the signals of a group to the locations of said further store, each location receiving that contribution relating to the path passing closest to the corresponding one of said spaced positions, and,
   (c) means for distributing at least a part of the contribution in said location, of the further store, to locations of the matrix store, corresponding to elemental regions of the body intersecting a line joining the corresponding one of said spaced positions to the said focus.

2. An apparatus according to claim 1 including means for providing control signals indicative of the angle between on the one hand the centerline of said divergent set of paths and on the other hand a perpendicular to said line parallel to lines of elemental regions, means for determining when said angle exceeds a predetermined value and means for changing, when said predetermined value is exceeded, to a further line parallel to lines of elemental regions at a different orientation in the matrix, for which the corresponding angle is less than the predetermined value.

3. An apparatus according to claim 1 including weighting means for modifying each electrical signal with contributions from other signals of the same group to produce further signals and means for weighting each further signal with a factor Cos $\gamma$, where $\gamma$ is the angle between the respective path and the centreline of the divergent set of paths.

4. An apparatus according to any one of claims 1, 2 and 3 including further weighting means for weighting each contribution allocated to a location of the matrix store by a factor related to D, the distance of the respective elemental region from the focus of the divergent set of paths.

5. An apparatus according to claim 4 in which the further weighting means weights the said contributions by a factor $1/D^2$.

6. An x-ray machine comprising:
   means for passing x-rays through a region and for deriving signals related to the manner in which the region attenuates said x-rays;
   means for providing a first set of storage locations which are related to the respective elements of a matrix of region elements;
   means for providing a second set of storage locations which are related to respective equidistantly spaced positions along a line which is substantially parallel to a number of linear groups of said matrix elements;
   means for storing in the second set of storage locations, modified signals which are functions of said first recited signals and relate to the respective directions of a fan of directions which has a focus outside the region and comprises directions which intersect said line at said equidistantly spaced positions;

means for distributing at least parts of the modified signals stored in the second set of storage locations to the storage locations of the first set such that a modified signal stored in a given location of the second set contributes to storage locations of the first set which are related to matrix elements which are along a line passing through both the focus of said fan and the position on said line which relates to said given location of the second set; and means for repeating said storing and said distributing for signals which relate to further fans of directions to thereby build up in the storage locations of the first set, an x-ray picture of said region, and means for displaying said x-ray picture.

7. A method comprising:

passing x-rays through a region and deriving signals related to the manner in which the region attenuates said x-rays;

providing a first set of storage locations which are related to the respective elements of a matrix of region elements;

storing, in a second set of storage locations which are related to respective equidistantly spaced positions along a line which is substantially parallel to linear groups of matrix elements, modified signals which are functions of said first recited signals and relate to the respective directions of a fan of directions which has a focus outside the region and comprises directions which intersect the line at said equidistantly spaced positions;

distributing at least parts of the modified signals stored in the second set of storage locations to the storage locations of the first set such that a modified signal stored in a given location of the second set contributes to storage locations of the first set which are related to matrix elements which are along a line passing through both the focus of said fan and the position on said first line related to said given location of the second set; and repeating said storing and distributing steps for signals which relate to further fans of directions to thereby build up in the storage locations of the first set, an x-ray picture of said region, and displaying said x-ray picture.

8. An x-ray machine comprising:

means for irradiating a region with x-rays and for deriving signals related to the manner in which the region attenuates the x-rays;

means for converting the signals to modified signals which are in groups arranged such that the modified signals of each group are related to directions which fan through the region and have a common focus, and each modified signal within a group is related to a respective one of the directions within the fan, there being a multiplicity of such fans having respective foci distributed around the region;

wherein if the region is divided conceptually into a rectangular array of elements and a number of lines of stretch are defined conceptually such that no two of them are parallel to each other but each is substantially parallel to a number of lines each of which passes through a number of said region elements, then the directions within each given fan intersect a respective one of said lines of stretch at points which are equidistant from each other and each of a number of fans so intersects the same line of stretch; and means for using said modified signals to build up an x-ray picture of said region and for displaying said picture.

9. A method of taking an x-ray picture of a region comprising the following steps each of which is machine-implemented:

irradiating a region with x-rays and deriving signals related to the manner in which the region attenuates the x-rays;

converting the signals to modified signals which are in groups arranged such that the modified signals of each group are related to directions which fan through the region and have a common focus, and each modified signal within a group is related to a respective direction within the fan, there being a multiplicity of such fans having respective foci distributed around the region;

wherein if the region is divided conceptually into a rectangular array of elements and a number of lines of stretch are defined conceptually such that no two of them are parallel to each other but each is substantially parallel to a number of lines each of which passes through a number of region elements, then the directions within any given one of said fans are arranged such that they intersect a respective one of said lines of stretch at points which are equidistant from each other and a number of fans so intersect the same line of stretch; and using said modified signals to build up an x-ray picture of said region and displaying said picture.

* * * * *

UNITED STATES PATENT AND TRADEMARK OFFICE
CERTIFICATE OF CORRECTION

PATENT NO. : 4,274,140
DATED : June 16, 1981
INVENTOR(S) : David M. Watson

It is certified that error appears in the above-identified patent and that said Letters Patent are hereby corrected as shown below:

Title page, between items "[76]" and "[21]", insert:

--[73] Assignee: E M I Limited, Hayes, England--.

Col. 5, line 63, change "arcs" to --arc--.

Signed and Sealed this

Tenth Day of August 1982

[SEAL]

Attest:

GERALD J. MOSSINGHOFF

Attesting Officer

Commissioner of Patents and Trademarks